United States Patent [19]

Gasson et al.

[11] 4,008,179
[45] Feb. 15, 1977

[54] CATALYST COMPOSITION

[75] Inventors: Edward James Gasson, Dollar, Scotland; Thomas Charles Krosnar, deceased, late of Polmont, Scotland, by Alena Krosnar, legal representative, Stanley Frederic Marrian, Fife, Scotland

[73] Assignee: BP Chemicals International Limited, London, England

[22] Filed: Oct. 1, 1975

[21] Appl. No.: 618,505

[30] Foreign Application Priority Data

Oct. 3, 1974  United Kingdom ............ 42915/74

[52] U.S. Cl. ................................ 252/437; 252/469
[51] Int. Cl.$^2$ ................... B01J 21/06; B01J 23/84; B01J 23/88; B01J 27/18
[58] Field of Search ................... 252/467, 469, 437

[56] References Cited

UNITED STATES PATENTS

| | | | |
|---|---|---|---|
| 3,551,470 | 12/1970 | Shaw et al. | 252/467 X |
| 3,595,911 | 7/1971 | Ball | 252/467 X |
| 3,709,829 | 1/1973 | Gasson | 252/467 X |
| 3,886,096 | 5/1975 | Li | 252/467 X |

*Primary Examiner*—W. J. Shine
*Attorney, Agent, or Firm*—Brooks Haidt Haffner & Delahunty

[57] ABSTRACT

A heat treated catalyst composition containing antimony and to which has been added an oxide or compound of molybdenum or tungsten in an amount such as to provide from 0.05 to 1.0 atom % of molybdenum or tungsten present, is further promoted by addition of an oxide or compound of uranium and/or vanadium in an amount such as to provide from 0.005 to 0.5 atom % of uranium or vanadium present.

7 Claims, No Drawings

CATALYST COMPOSITION

The present invention relates to catalyst compositions and in particular to catalyst compositions containing antimony, for use in catalysing reactions of organic compounds.

Catalyst compositions containing antimony in the form of an oxide or oxide compositions are well-known for use in catalysing reactions of organic compounds. Thus, for example, it is well-known to use such catalysts which also contain other metals combined in the form of oxides or oxide compositions to catalyse the oxidation of olefins such as propylene or isobutene to produce the corresponding unsaturated aliphatic aldehydes such as acrolein or methacrolein or the unsaturated aliphatic carboxylic acids such as acrylic or methacrylic acids or to catalyse the oxidation of the unsaturated aliphatic aldehydes themselves to produce such corresponding acids or to catalyse the conversion of such olefins and/or aldehydes to the corresponding unsaturated aliphatic nitriles such as acrylonitrile or methacrylonitrile by reaction with ammonia and molecular oxygen or to catalyse the oxidative dehydrogenation of mono-olefins to produce diolefins. In particular it is known from British Patent Specification No. 876,446 (The Distillers Company Limited) to produce acrylonitrile or methacrylonitrile by a process which comprises reacting at an elevated temperature in the vapour phase propylene or isobutene with oxygen and ammonia over an oxidation catalyst comprising (i) a mixture of the oxides of antimony and tin and/or (ii) a compound of antimony, tin and oxygen. In U.S. Pat. No. 3,914,278 there is described and claimed a process for the production of acrylonitrile which comprises reacting at an elevated temperature in the vapour phase, propylene, molecular oxygen and ammonia over a catalyst which is an oxide composition comprising antimony, tin and titanium with, in addition, one or more of the oxides of the metals copper, magnesium, zinc, vanadium, uranium, chromium, manganese, molybdenum, tungsten, iron, cobalt, nickel, indium, arsenic, bismuth and tellurium.

According to the invention described in co-pending U.S. patent application Ser. No. 585,481 filed June 10, 1975, it has now been found that with such antimony based catalysts it is possible to promote their activity by the addition of certain elements, namely molybdenum and/or tungsten, in a compounded form. According to the invention of this co-pending application it is found that only by incorporation of the additional elements in amounts within a narrow defined range i.e. from 0.05 to 1.0 atom % is any benefit obtained.

It is advantageous commercially to operate acrylonitrile-producing reactors at as low a temperature as possible in order to preserve the metals of construction from damage by excessive temperatures. This is particularly important if the metals are in contact with a heat transfer salt. It is often possible to make minor alterations to the optimum reaction temperature of a catalyst by altering its preparation. There is, however, a limit for any specific catalyst, beyond which it will not provide its maximum possible acrylonitrile yield. Thus, with some catalysts a compromise may be necessary and this will result in a decreased acrylonitrile productivity.

It has now been found that antimony based catalysts of the type described in co-pending application Ser. No. 585,481 filed June 10, 1975 and containing molybdenum and/or tungsten can be made to operate at lower optimum reaction temperatures, without significant loss in acrylonitrile yield if they also contain trace quantities of uranium or vanadium oxide compositions.

Thus according to the present invention, there is provided a catalyst composition suitable for catalysing the reaction of organic compounds which comprises an oxide composition containing antimony and which has been heat-treated at a temperature between 700° and 900° C in a molecular oxygen containing gas and to which has been added, either before or subsequent to the heat treatment, an oxide or compound of molybdenum or tungsten or mixtures thereof, in amount such as to provide from 0.05 to 1.0 atom % as hereinafter defined of molybdenum and/or tungsten, in the catalyst composition, together with an oxide or compound of uranium and/or vanadium in amount such as to provide from about 0.005 to 0.5 atom % as hereinafter defined of uranium and/or vanadium in the catalyst composition.

By the term "atom %" herein is meant the quotient $$\frac{100 \times \text{number of atoms of the additional metal}}{\text{Total number of metal atoms in the oxide composition}}.$$

It is preferred to add an oxide or compound of molybdenum and/or tungsten to the heat-treated oxide composition in an amount such as to provide from 0.1 to 0.6 atom % of the molybdenum and/or tungsten. It is preferred to add an oxide or compound of uranium or vanadium in an amount such as to provide from about 0.01 to 0.3 atom % of uranium and/or vanadium.

The oxide composition containing antimony may also contain one or more additional metals combined in the form of oxide or oxide compositions. Suitable metals, among many other, include tin, titanium, copper, magnesium, zinc, chromium, manganese, iron, cobalt, nickel, indium, arsenic and tellurium. Catalyst compositions found to be particularly suitable for catalysing the reaction of propylene, molecular oxygen and ammonia to produce acrylonitrile are those containing antimony, with additional metals chosen from tin, iron, copper, arsenic and titanium.

When such additional metals are present the oxide composition may be regarded as either a mixture of the oxides of the various metals or as oxygen-containing compounds of such metals; under the reaction conditions either or both forms may be present and may be prepared by any known method such as by intimately mixing the oxides or compounds yielding the oxides on heating, or coprecipitation of the oxides, hydrated oxides or insoluble salts from an aqueous solution. The oxide composition is dried (if necessary), pelleted and heated in a molecular oxygen containing gas at a temperature between 700° and 900° C. The duration of the heat treatment may vary but is usually about 16 hours or more.

Thus, the complete composition may be prepared by precipitation of the oxides, hydroxides, etc. of all the components and heat treatment within the range 700° to 900° C. In this embodiment the molybdenum or tungsten components may be added to the remaining composition during the final washing stages of the latter in the form of solid compounds or aqueous solutions thereof. Alternatively the constituents excluding molybdenum and/or tungsten together with the uranium and vanadium may first be prepared and heat-treated, then the heat-treated composition may be immersed in a solution of a heat-decomposable compound of molybdenum and/or tungsten, e.g. ammonium molybdate, tungstate or phosphate, molybdophosphoric acid or tungstophosphoric acid, followed by immersion of the composition in a solution of a heat decomposable compound of uranium and/or vanadium. Alternatively the heat decomposable compound of uranium or vanadium may be mixed in solution with the heat decomposable salts of molybdenum or tungsten. In a third method, the molybdenum or tungsten additive together with the uranium or vanadium additive may be introduced into the catalyst by passing the vapour of a suitable compound of the additive e.g. molybdic oxide over or through a bed of the catalyst at an elevated temperature.

The present invention is described in further detail with reference to the following Examples.

EXAMPLE 1

A basic catalyst was prepared by the following method to give atomic proportions Sb/Sn/Cu/Fe/Ti = 3/1/0.25/0.25/0.25.

Antimony trioxide (438 parts by weight) was added to a heated (100° C) stirred mixture of water (1500 parts) and 70% nitric acid (531 parts), and this was followed by powdered tin (118.6parts) added over 10 minutes. After cooling, the mixutre was filtered and the cake was suspended in water (1300 parts). To the stirred mixture was added $Cu(NO_{(NO3)})_2 \cdot 3H_2O$ (60.6 parts) in water (200 parts), $Fe(NO_3)_3 \cdot 9H_2O$ (101.4 parts) in water (200 parts), and n-butyl titanate (83.8 parts) in dilute nitric acid (17% concentration, 240 parts), and the temperature was raised to 40° C. Aqueous ammonia was added until the pH was 6.3, and after stirring for 15 min. the mixture was cooled to room temperature and filtered. The cake was re-suspended in water (2600 parts), filtered and dried. After pelleting to cylinders of 4 mm diameter and 4 mm length, the pellets were heat-treated in a furnace in which the temperature was raised at 22° C per hour and in which an air stream was injected at a rate of 50 liters/hour/Kg catalyst. When a temperature of 850° C was reached the pellets were maintained at this temperature for 16 hours.

EXAMPLE 2

The basic catalyst prepared as described in Example 1 was soaked in a 1% aqueous solution of ammonium molybdate for 16 hours followed by draining and drying to give a composition having an atom ratio Sb : Sn : Cu : Fe : Ti : Mo = 3:1 : 0.25 : 0.25 : 0.25 : 0.015.

EXAMPLE 3

The basic catalyst prepared as described in Example 1 was soaked in an aqueous solution containing 1% ammonium molybdate and 0.23% of uranyl acetate for 12 hours followed by draining and drying to give a composition having an atom ration Sb : Sn : Cu : Fe : Ti : Mo : U = 3:1 : 0.25 : 0.25:0.25 : 0.011 : 0.001, the uranium content being 0.02 atom percent

EXAMPLE 4

The basic catalyst prepared as described in Example 1 was soaked in an aqueous solution containing 1% ammonium molybdate and 0.32% ammonium metavanadate for 12 hours followed by draining and drying to give a composition having an atom ration Sb : Sn : Cu : Fe : Ti : Mo : V = 3:1 : 0.25 : 0.25 : 0.25 : 0.009 : 0.005, the vanadium content being 0.1 atom percent.

EXAMPLE 5

The basic catalyst prepared as described in Example 1 was soaked in a molybdenovanado phosphoric acid ($H_5(PMo_{10}V_2O_{40}) \cdot 32H_2O$) solution (1.3% aqueous for 16 hours) to give a composition having an atom ration Sb : Sn : Cu : Fe : Ti : Mo : V : P = 3 : 1 : 0.25 : 0.25 : 0.25 : 0.014 : 0.0045 : 0.0015.

EXAMPLE 6

The basic catalyst prepared as described in Example 1 was soaked in a 0.64% aqueous solution of ammonium metavanadate, drained, dried and heated to 830° C for 12 hours, soaked in a 1% aqueous solution of ammonium molybdate, drained and dried to give a composition having an atom ration Sb : Sn : Cu : Fe : Ti : V : Mo = 3 : 1 : 0.25 : 0.25 : 0.25 : 0.017 : 0.011.

All of the catalyst compositions of the above Examples 2 – 6 were tested as follows:

A mixture of propylene, ammonia, air and steam in volume ratio (calc. at N.T.P.) of 6 : 6.5 : 68 : 19.5 was passed over the catalyst contained in a glass reactor immersed in a heating bath; the contact time was 8 seconds. The following table shows the conditions under which a maximum acrylonitrile yield was obtained.

| Example | Bath Temp ° C | Yields of products - % molar on propylene fed | | | | | Acrylonitrile Efficiency % |
| | | Acrylonitrile | Acrolein | Hydrogen Cyanide | Carbon Dioxide | Propylene | |
| --- | --- | --- | --- | --- | --- | --- | --- |
| 2 | 466 | 74.3 | 0.9 | 5.9 | 8.5 | 3.4 | 76.9 |
| 3 | 450 | 74.3 | 0.9 | 5.8 | 9.3 | 2.4 | 76.1 |
| 4 | 448 | 73.3 | 0.7 | 5.9 | 11.5 | 1.8 | 74.6 |
| 5 | 455 | 72.9 | 1.4 | 5.8 | 8.4 | 4.2 | 76.1 |
| 6 | 449 | 74.8 | 1.1 | 5.6 | 9.3 | 2.2 | 76.5 |

Comparison of the results recorded above indicated that the use of catalyst compositions containing traces of uranium or vanadium result in lowering of the optimum temperature of from 11 to 18° C without loss of yield or efficiency.

We claim:

1. A catalyst oxide composition suitable for catalysing the reaction of organic compounds which consists essentially of oxygen and the metal elements antimony, tin, copper, iron and titanium, and molybdenum or tungsten, and uranium or vanadium, and which has been heat treated at a temperature between about 700° and 900° C in a molecular oxygen-containing gas either before or after addition of the molybdenum or tungsten.

2. A catalyst oxide composition as defined in claim 1 which consists essentially of oxygen and the metal elements antimony, tin, copper, iron, titanium, molybdenum and uranium.

3. A catalyst oxide composition as defined in claim 1 which consists essentially of oxygen and the metal elements antimony, tin, copper, iron, titanium, molybdenum and vanadium.

4. A catalyst oxide composition as defined in claim 1 which additionally contains phosphorus.

5. A catalyst oxide composition as defined in claim 1 wherein the amount of uranium or vanadium is from about 0.005 to 0.5 atom percent.

6. A catalyst composition as claimed in claim 1 wherein the amount of molybdenum and/or tungsten in the catalyst composition is from 0.1 to 0.6 atom %.

7. A catalyst composition as claimed in claim 1 wherein the amount of uranium and/or vanadium in the catalyst composition is from 0.01 to 3.0 atom %.

* * * * *

UNITED STATES PATENT AND TRADEMARK OFFICE
CERTIFICATE OF CORRECTION

PATENT NO. : 4,008,179

DATED : February 15, 1977

INVENTOR(S) : EDWARD JAMES GASSON; THOMAS CHARLES KROSNAR, deceased, by Alena Krosnar, legal representative, and STANLEY FREDERIC MARRIAN It is certified that error appears in the above-identified patent and that said Letters Patent are hereby corrected as shown below:

Col. 3, line 29, correct the spelling of "mixture"

line 31, "$Cu(NO_{(NO3)2}$" should read --$Cu(NO_3)_2$--

Signed and Sealed this

Twenty-fifth Day of October 1977

[SEAL]

Attest:

RUTH C. MASON
Attesting Officer

LUTRELLE F. PARKER
Acting Commissioner of Patents and Trademarks